United States Patent [19]

Sepaniak et al.

[11] Patent Number: 5,176,881
[45] Date of Patent: Jan. 5, 1993

[54] FIBER OPTIC-BASED REGENERABLE BIOSENSOR

[75] Inventors: Michael J. Sepaniak; Tuan Vo-Dinh, both of Knoxville, Tenn.

[73] Assignee: The University of Tennessee Research Corporation, Knoxville, Tenn.

[21] Appl. No.: 765,579

[22] Filed: Sep. 25, 1991

Related U.S. Application Data

[63] Continuation of Ser. No. 392,439, Aug. 11, 1989, abandoned.

[51] Int. Cl.⁵ .............................................. G01N 21/77
[52] U.S. Cl. .................................. 422/82; 422/82.06; 356/39; 128/634
[58] Field of Search ................. 422/68.1, 82.05, 82.06, 422/82.09, 82.08, 82; 436/172; 128/633-636, 673; 356/39-41

[56] References Cited

U.S. PATENT DOCUMENTS

| | | | |
|---|---|---|---|
| 4,200,110 | 4/1980 | Peterson et al. | 128/634 |
| 4,265,249 | 5/1981 | Schindler et al. | 128/635 |
| 4,344,438 | 8/1982 | Schultz | 128/634 |
| 4,622,974 | 11/1986 | Coleman et al. | 128/634 |
| 4,682,895 | 7/1987 | Costello | 356/402 |
| 4,710,623 | 12/1987 | Lipson et al. | 250/227 |
| 4,765,339 | 8/1988 | Jones | 128/632 |
| 4,785,814 | 11/1988 | Kane | 128/634 |
| 4,800,886 | 1/1989 | Nestor | 128/634 |
| 4,803,992 | 2/1989 | Lemelson | 126/634 |
| 4,844,887 | 7/1989 | Galle et al. | 422/65 |
| 4,929,561 | 5/1990 | Hirschfeld | 436/116 |
| 4,929,562 | 5/1990 | Anderson et al. | 436/126 |
| 4,954,318 | 9/1990 | Yafuso et al. | 422/59 |

OTHER PUBLICATIONS

"Development of Antibody-Based Fiber-Optic sensors for Detection of a Benzo[a]-pyrene Metabolite", By Bruce J. Tomberg, Michael J. Sepaniak and Jean Pierre Alarie, Tuan Vo-Dinh and Regina M. Santella, Reprinted from Analytical Chemistry, 1988, 60, 1901.

"The Clinical Use of Laser-Excited Fluorometry", by Michael J. Sepaniak. Reprinted from Clinical Chemistry, 31, 679 (1985).

Primary Examiner—James C. Housel
Assistant Examiner—Jeffrey R. Snay
Attorney, Agent, or Firm—Luedeka, Hodges, Neely & Graham

[57] ABSTRACT

A fiber optic-based regenerable biosensor. The biosensor is particularly suitable for use in microscale work in situ. In one embodiment, the biosensor comprises a reaction chamber disposed adjacent the distal end of a waveguide and adapted to receive therein a quantity of a sample containing an analyte. Leading into the chamber is a plurality of capillary conduits suitable for introducing into the chamber antibodies or other reagents suitable for selective interaction with a predetermined analyte. Following such interaction, the contents of the chamber may be subjected to an incident energy signal for developing fluorescence within the chamber that is detectable via the optical fiber and which is representative of the presence, i.e. concentration, of the selected analyte. Regeneration of the biosensor is accomplished by replacement of the reagents and/or the analyte, or a combination of these, at least in part via one or more of the capillary conduits. The capillary conduits extend from their respective terminal ends that are in fluid communication with the chamber, away from the chamber to respective location(s) remote from the chamber thereby permitting in situ location of the chamber and remote manipulation and/or analysis of the activity with the chamber.

5 Claims, 3 Drawing Sheets

FIBER OPTIC-BASED REGENERABLE BIOSENSOR

This is a continuation of Ser. No. 07/392,439, filed Aug. 11, 1989 now abandoned.

FIELD OF THE INVENTION

The present invention relates to methods and apparatus for the microanalysis of a fluid and particularly those methods and apparatus using optical fibers.

BACKGROUND OF THE INVENTION

Fiber optics have had a significant impact on many areas of science and technology, not least of which are the areas of physical and chemical sensing. Sensors that measure the intrinsic absorbance, scattering or fluorescence of an analyte are generally referred to as optical sensors. Better analytical selectivity is achieved with a fiber optic chemical sensor (FOCS). The spectroscopic signals obtained with FOCS are the result of specific interactions between the analyte of interest and a reagent phase that is immobilized at the sensing end of the optical fiber. These interactions often take the form of chemical reactions between analyte and reagent that result in a colored or fluorescent product.

Because of their selectivity and versatility with regard to reagent-analyte interactions, FOCS have received much more attention than the optical-type fiber optic sensors. Most reports of FOCS involve the measurement of small molecules (e.g., $CO_2$, $NH_3$, metal ions and pH). More recently, FOCS have been applied to the measurement of large macromolecules through the immobilization of highly selective bioreceptor affinity reagent phases.

In certain prior art, the reagent phase of a FOCS has been immobilized by covalent attachment to the fiber surface, entrapped in a membrane sealed compartment, or incorporated into a polymer matrix at the distal end of the optical fiber.

These configurations allowed a highly sensitive and selective analysis of chemicals in biological fluids such as blood and other body fluids. These analyses, although selective and sensitive, may only be performed once before regeneration of the reagent was required. This regeneration was time consuming and required the removal of the sensor from the biological fluid.

It is therefore an object of the present invention to provide a regenerable, i.e. semi-continuous, fiber optic-based sensor.

It is another object of the present invention to provide a regenerable fiber optic-based sensor useful in in situ analyses.

It is another object of the present invention to provide a regenerable fiber optic-based sensor small enough to be placed into a biological system, e.g., through a hypodermic needle.

SUMMARY OF THE INVENTION

The present invention provides for a regenerable sensor for the microanalysis of the presence and/or concentration of at least one component (an analyte) of a multi-component fluid (a sample). The sensor comprises a probe defining a reaction chamber for receiving a portion of the fluid investigation. Means are provided for selecting the volume of sample introduced into the reaction chamber, for introducing reagents into the chamber, for applying an incident light beam to the chamber, for detecting fluorescence or the like emanating from the chamber and/or for selectively introducing and/or withdrawing all or portions of the contents of the chamber to regenerate the sensor for further or subsequent analyses. Optical means are provided for directing radiant energy into and out of the chamber and converting the same to a value representative of the presence, e.g. molar concentration, in the chamber of an analyte under investigation.

In a preferred embodiment, the present biosensor comprises a probe of a size suitable for in situ analyses of human or animal body fluids. Further, in a preferred embodiment, the probe comprises a bundle of capillary conduits spaced about an optical fiber, the respective one ends of which terminate in a common plane and are capped by a fritted cover. The conduits and optical fiber are sealed in the cover with their ends spaced from the covering end wall of the cover by a distance sufficient to define a reaction chamber between the conduit ends and such end wall. A typical volume of such reaction chamber is less than 1 $\mu l$. Selected ones of the conduits are connected at their ends remote from the probe to aspiration means, waste removal means, or reagent introduction means. The remote end of the optical fiber is connected to optical means for generating a pulsed or continuous incident light beam, for detecting radiation emanating from the reaction chamber, and for analyzing such emanating radiation. Typical conduits are of about 200 $\mu m$ I.D. and may range in length as required, a length of about 100 cm being common.

In accordance with the method of the present invention, the probe is introduced to a source of fluid suspected of containing an analyte under consideration. A sample of the fluid enters the reaction chamber through the fritted cover either by migration or in response to aspiration. The reaction chamber may contain reagent(s) before the analyte enters the chamber, but preferably, one or more reagents are introduced into the chamber via one or more of the capillary conduits after the analyte has been aspirated into one of the conduits. These reagent(s) may be solid (e.g. microspheres), may be bound to a solid (e.g. an antibody bound to microspheres) or may be a liquid. The reagent(s) may be caused to flow through the chamber or to reside for a selected time in the chamber. The sampled analyte is then transported to the chamber containing the reagents. The reagent(s) react with the analyte while these materials are in the chamber. As desired, the contents of the chamber, usually after reaction, may be washed by means of fluids introduced into the chamber via a capillary conduit, to remove interferants with the reaction and/or with the desired radiant energy generation. The wash fluid carrying the interferants may be removed through a conduit (or conduits) whose ends are fritted against withdrawal of selected material(s) from the chamber or may be expelled through the frit that defines the reaction chamber. By suitable manipulations, these operations can be performed without removing the signal generating analyte from the field of view of the optical fiber.

In a preferred embodiment of the invention, a sample of a biological fluid is drawn through the reaction chamber and into a capillary conduit. The volume of the sample is several times, e.g. about fifteen or twenty times, the volume of the chamber. An affinity reagent is introduced into the chamber through a second capillary conduit at a volume sufficient to bind all of the analyte of interest contained in the sample. The sample is returned through the first capillary conduit and then through the reaction chamber. The analyte in the sample binds with the affinity reagent in the chamber to form an affinity reaction product. As the sample passes through the chamber, the analyte reacts with the affinity reagent thereby accumulating and concentrating the analyte in the chamber. If the reaction product fluoresces, the product is excited by a beam of light and the fluorescence is detected and analyzed. If the affinity reaction product is not fluorescent, then the excess sample and reagent are removed from the reaction chamber by a third capillary conduit and a second reagent tagged with a fluorescent label is introduced into the chamber. A light beam of a wavelength to excite the affinity product to fluorescence is introduced into the reaction chamber and induces the fluorescence. The fluorescence beam is then detected and analyzed. Thereafter, the entire contents, or selected portions thereof may be removed from the reaction chamber and the sensor is regenerated by repeating all or a portion of the above operations.

Regeneration of the biosensor is in part determined by the preceding reaction protocol. In the instance where the reagent is expended in the course of the reaction, at the end of a reaction protocol the entire contents of the reaction chamber may be withdrawn in preparation for repeating the protocol. As desired, the chamber may be flushed between protocols. In the instance where the reagent is not expended in the course of the reaction, e.g. in certain cases, antibodies bound to microspheres, at the end of a reaction protocol the contents of the reaction chamber except the nonspent reagent are withdrawn, as by aspiration through a conduit whose end is fritted. The reagent remaining in the reaction chamber may be washed, if desired, without its removal from the reaction chamber. In any event, the nonspent reagent remains available in the chamber for use in a subsequent reaction protocol. These regeneration actions may be repeated as desired with the probe remaining in situ, thereby making the present biosensor capable of semi-continuous service.

In a typical reaction protocol, when the analyte and reagents react there is commonly formed a reaction product. Desirably this reaction product is fluorescent. In the instance where the reaction product fluoresces, the intensity of the fluorescence, as measured by the optical system referred to hereinabove is taken as a measure of the concentration of the analyte under surveillance. In the event the reaction product does not "naturally" fluoresce, a further reagent may be introduced to the reaction chamber by way of one of the conduits to supply a label composition to the reaction product, such label being capable of fluorescing when subjected to an incident light beam. In this latter situation, when the label has attached to the analyte under consideration, a laser directs a beam of light along the optical fiber into the reaction chamber. This light activates the fluorescing labeled product and the resultant intensity of the fluorescence is again taken as a measure of the concentration of the moiety under investigation.

In one embodiment, reagent introduced into the reaction chamber comprises microspheres. These microspheres may be inherently reactive, i.e. be made up of a reagent, or they may be inert and be coated with a reagent, e.g. an antibody, that is specific for the analyte of interest in the sample. Such microspheres may be on the order of less than about 7 μm in diameter and are readily flowable through a capillary conduit.

The probe of the present invention preferably is a microscale probe small enough to fit within the barrel of a medium sized hypodermic needle and therefore is readily positionable within a body for in situ analyses of the fluid of interest, e.g., blood or the fluid surrounding a tumor. However, the apparatus is not restricted to bioanalytical applications. Environmental and industrial applications where in situ, remote measurements are necessary are envisioned. The term "microscale" as used herein refers to methods and apparatus capable of the reproducible measurement of components in sample volumes of less than 20 μl.

Light introduced into the reaction chamber through the optical fiber may be of a particular wavelength to excite the reaction product or sandwich compound to cause fluorescence. The light can be pulsed and of short duration to minimize photodegradation. As is characteristic of fluorescence, the measured signal is at a longer wavelength than the excitation light. This fluorescence is transmitted by the optical fiber to detection and analysis means remote from the probe. Analysis of the fluorescence signal provides an indication of the concentration of the component of interest in the biological fluid.

The present invention provides an ability to almost continuously monitor the concentration of one or more components of interest in the biological fluid. This allows the monitoring of, for example, drug dosages in the blood at very low levels, the presence of hormones or other natural biological molecules or any other compound of interest in biological fluids. This is a qualitative and quantitative improvement over the "one-shot" approach of previous fiber optic-based chemical sensors and over the macroanalytical techniques such as blood tests. Since the sensor is small enough to be placed in a blood stream, the analysis may be conducted and the sensor may be regenerated in vivo.

BRIEF DESCRIPTION OF THE DRAWINGS

The present invention may be best understood by reference to the following detailed description of an exemplary embodiment when considered in conjuction with the drawings in which.

DETAILED DESCRIPTION OF THE DRAWINGS

Figure 1:
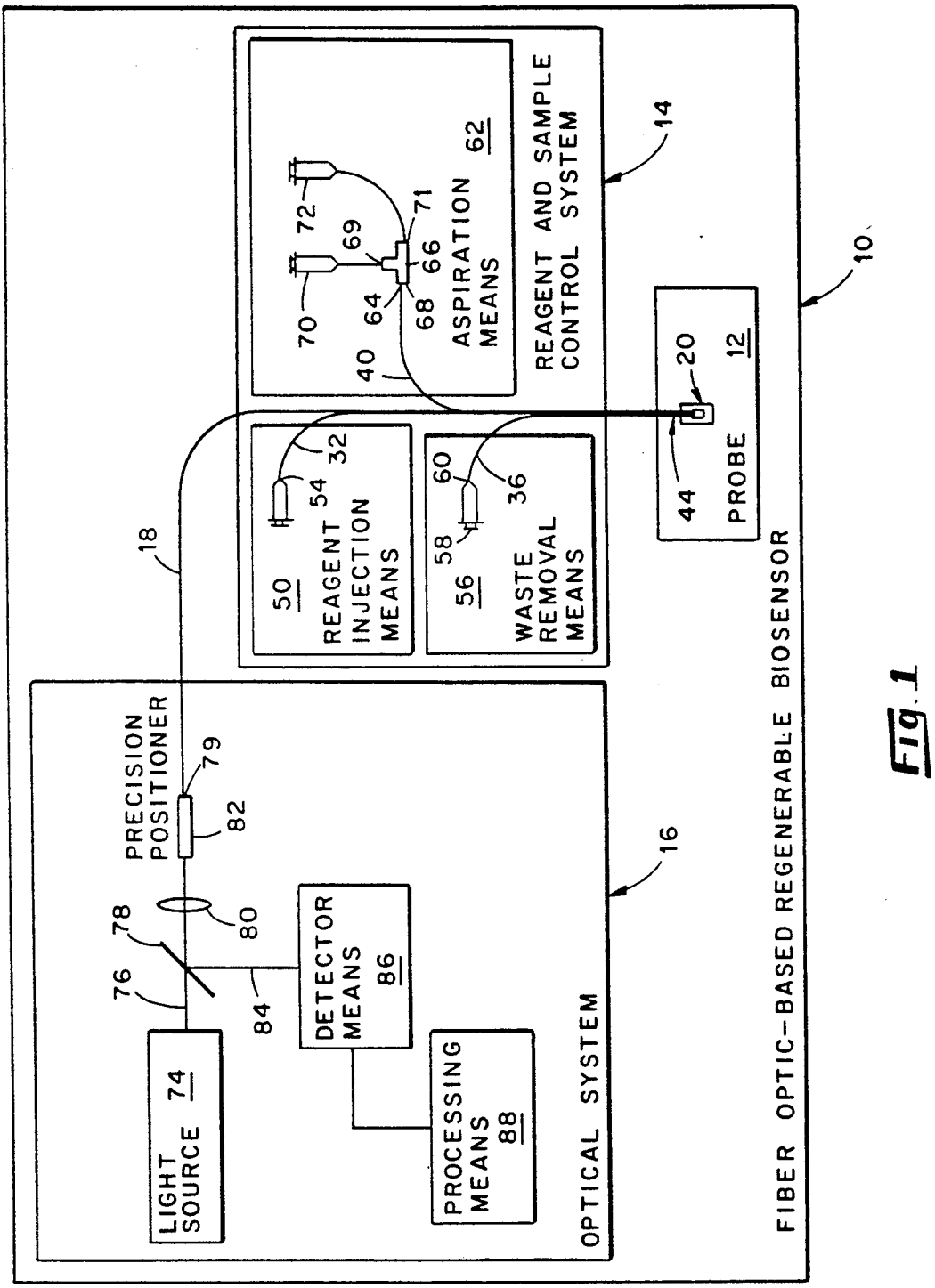
FIG. 1 is a somewhat diagrammatical view of an apparatus for using a fiber optic-based regenerable biosensor.
Figure 3:
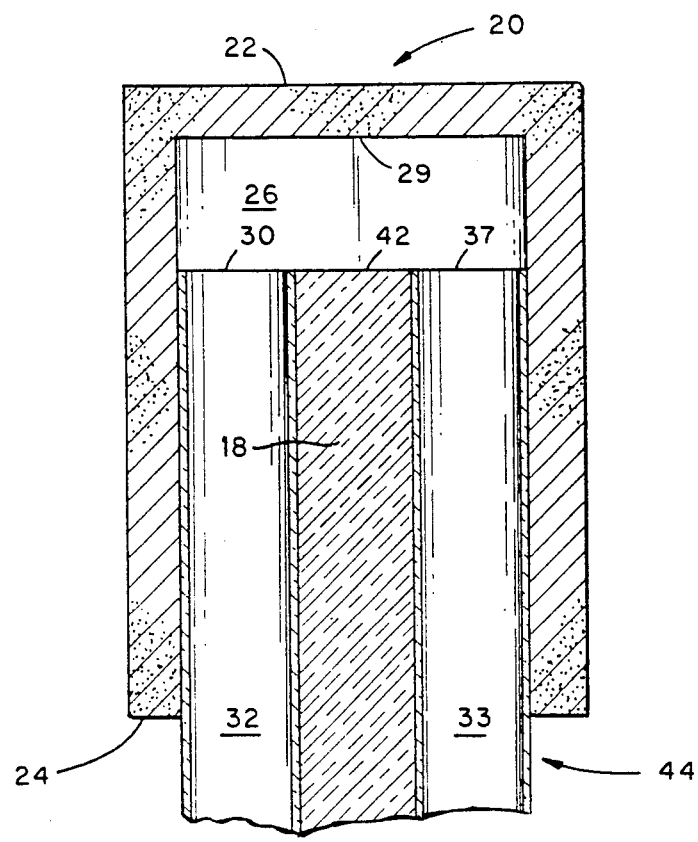
FIG. 3 is a cross-sectional view of the probe depicted in FIG. 2 taken along line 3—3 and viewed in the dirction of the arrows.
Figure 4:
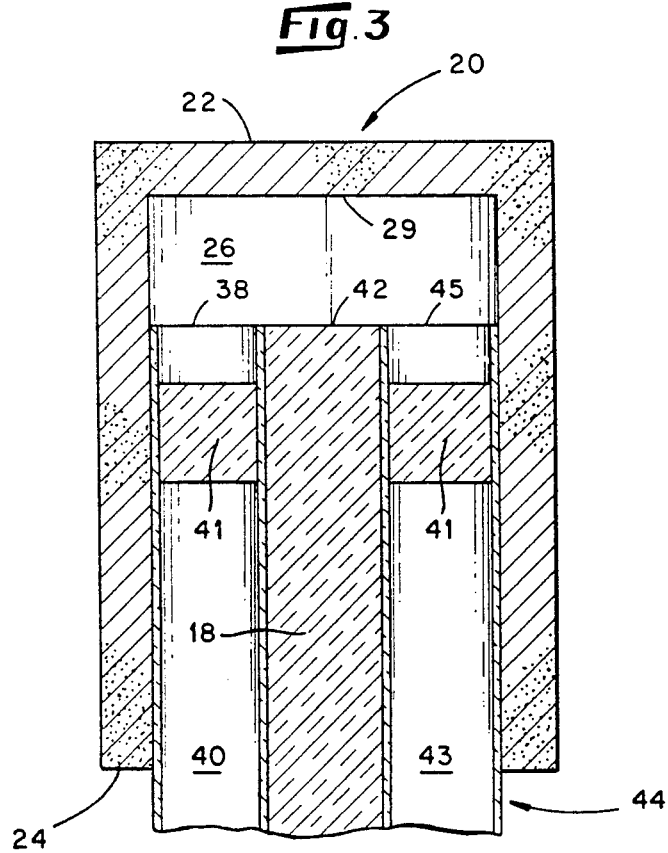
FIG. 4 is a cross-sectional view of the probe depicted in FIG. 2 taken along the line 4—4 and seen in the direction of the arrows.

Referring now to the drawings in which like reference characters designate like or corresponding parts throughout the several views, there is shown in FIG. 1 an apparatus for using a fiber optic-based regenerable biosensor 10 embodying the present invention. Basically, the apparatus 10 includes three parts, a probe 12, a reagent and sample control system 14 and an optics system 16. The parts are interconnected by an optical fiber 18.

Figure 2:
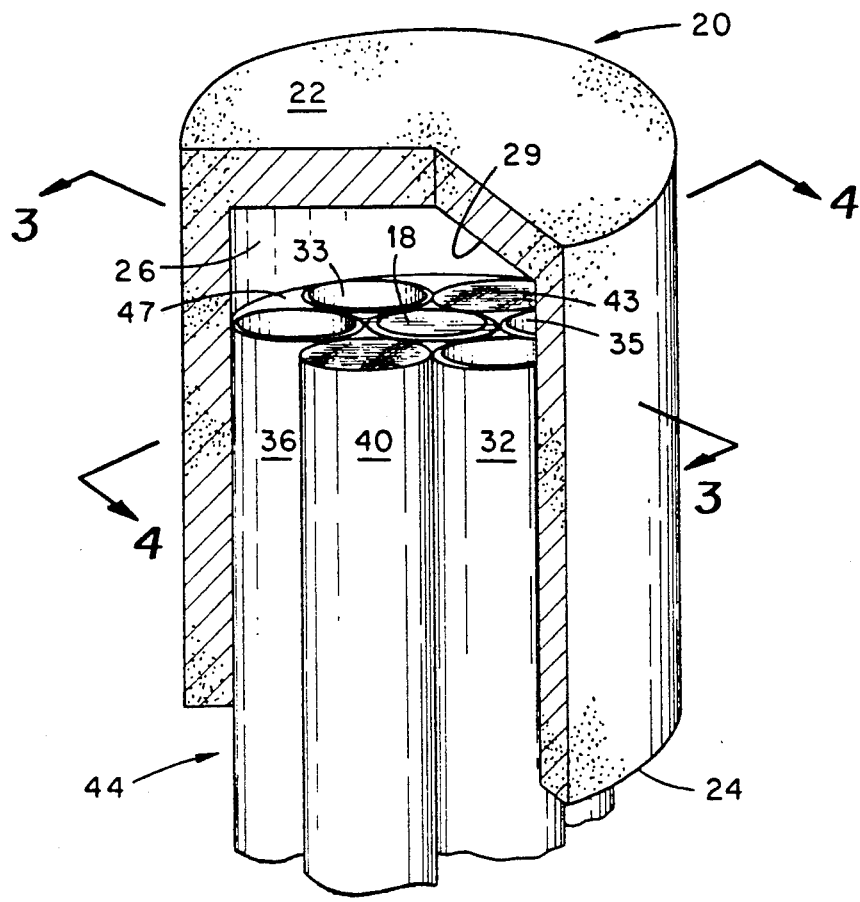
FIG. 2 is a cut-away perspective view of a probe for use in a fiber optic-based regenerable biosensor.

A cut-away perspective of the probe 12 is shown in FIG. 2. The probe 12 includes a fritted stainless steel member 20 that is preferably a cylinder approximately 4 mm in lenght and 2 mm in diameter. The distal end 22 of membert 20 is designed to be placed in the fluid of interest. A cylindrical hollow chamber 26 is provided coaxially with the length of the member 20 and extends from the innermost end 24 of the member 20 a distance, e.g. about 3 mm, to form a cylindrical cup-like chamber 26 and provide the fritted stainless steel, or other material such as titanium, member 20 with a bottom thickness from an interior flat face 29 to the fluid end 22 of about 0.3 mm and a wall thickness of about 0.3 mm. The porosity of the fritted material is fixed to retain solid material of about 5 $\mu$m in diameter and typically has a pore size greater than 1 $\mu$m.

The probe 12 also includes one end 30 of at least one reagent conduit 32, one end of at least one waste conduit 36, one end 38 of at least one aspiration conduit 40 and one end 42 of the optical fiber 18. The ends of certain conduits can be supplied with fritted closures 41, preferably prepared of porous teflon, for preventing the comunication of solid material into the interior of the conduits during rinsing or reagent addition. The use of fritted ends is not necessary when these steps are performed with waste conduits 36 sealed an the reagent flow is through member 20. The conduits of a preferred embodiment of the invention are prepared from capillaries with an outside diameter of about 300 $\mu$m and inside diameter of about 200 $\mu$m. In a preferred embodiment, the optical fiber 18 has a diameter of between about 200 $\mu$m and about 600 $\mu$m.

In the depicted embodiment, there are provided a further reagent conduit 33, a further waste conduit 35 and a further aspiration conduit 43, the respective ends 37, and 45, respectively, of which terminate in the chamber 26 of the fritted member 20.

The reagent conduits 32 and 33, waste conduits 35 and 36, aspiration conduits 40 and 43 and optical fiber 18 are gathered together into a parallel bundle 44 with the fiber 18 occupying a central position and the several conduits being aligned in a parallel axial fashion to the central fiber 18. In the depicted embodiment of the present invention, the several conduits are arranged in a hexagonal pattern about the central fiber 18. The ends of the several conduits which terminate in the chamber 26 are aligned to be flush with one another and spaced apart from the inner end surface 27 of the fritted member 20 to define the chamber 26 so as to form a flat probe end of the bundle 44.

As shown, the cup-like member 20 may be demountably placed over the bundle 44 with the bundle 44 being contained within the chamber 26 of the member 20. In any event a sealant 47 is provided about the ends of the several conduits and the inner wall of the chamber 26 to restrict the flow of material in or out of the chamber 26 to the passageways provided by the several conduits. thus, the reaction chamber 26 is of suitable dimensions to receive a sample for analysis and any necessary reagents for analyzing an analyte of choice in such sample. In the depicted embodiment of the present invention, the ends of the conduits are positioned at a distance ob between about 0.2 mm and about 0.4 mm from the interior flat face 29 of the member 20. This provides a reaction chamber 26 with a volume of less than about 1 $\mu$l.

The probe 12 is connected by the conduit 32 to a reagent and sample control system 14 which includes a reagent injection means 50, for example, a tuberculin syringe, connected to a reagent end 54 of the reagent conduit 32 thereby placing the reagent injection means 50 in fluid communication with the reaction chamber 26. In the event there are multiple conduits 32 and 33, for example, each reagent conduit is connected to its own syringe, and each syringe is filled with its own reagent. As will be described in greater detail hereinafter, each reagent is chosen to react specifically with a particular constituent of the fluid of interest. Depending upon various factors such as the analyte sought to be analyzed, the number of reagents, if any, needed to effect the desired reaction in the reaction chamber 26, an additional reagent injection means may be employed.

The reagent and sample control system 14 also includes a waste removal means 56 which is connected to the waste end 60 of the waste conduit 36 thereby providing fluid communication between the waste removal means 56 and the reaction chamber 26. The waste removal means 56 may comprise, for example, a tuberculin syringe 58 which is operable to remove waste material from the reaction chamber 26 via the conduit 36. In the depicted embodiment of a probe as in FIG. 2, an additional waste conduit 35 is provided and is connected to its own waste removal means (not shown) which may be identical to the waste removal means 56.

An aspiration means 62 is also included in the reagent and sample control system 14. The aspiration means 62 is in fluid communication with the reaction chamber 26 by reason of its connection of the aspiration end 64 of the aspiration conduit 40. The depicted aspiration means 62 includes a T-shaped connector 66 the first end 68 of which is connected to the aspiration end 64 of the aspiration conduit 40. A second end 69 of the connector 66 is connected to first aspiration means 70, for example, a tuberculin syringe, for withdrawing fluid from the reaction chamber 26. The third end 71 of the connector 66 is connected to further aspiration means 72, for example, a tuberculin syringe, for quantitatively returning a quantity of the withdrawn fluid to the aspiration conduit 40 thence to the reaction chamber 26. In operation, the aspiration means 62 creates a partial vacuum in the reaction chamber 26 and thereby draws fluid from a reservoir of the fluid of interest into the reaction chamber 26. The withdrawn fluid fills the aspiration conduit 40 past the T-shaped connector 66 toward the syringe 70. Thereafter, the syringe 72 is operated to pressurize the conduit 40 and return to the reaction chamber 26 only that fluid that is in the aspiration conduit 40 between the connector 66 and the reaction chamber 26. Therefore, a repeatable quantity of fluid may be introduced into the reaction chamber 26. The operation of the aspiration means 62 as well as the reagent and sample control system will be further described hereinafter.

The probe 12 is connected by the optical fiber 18 to an optical system 16 which includes a light source 74, for example, a twenty milliwatt Cyconic argon ion laser producing radiation at 488 nm. A laser beam 76 is transmitted to a beam splitter 78, e.g. a 25 mm diameter mirror with a 2 mm hole bored in its center, which transmits the laser beam 76 toward a lens 80 which focuses the laser beam 76 onto the end 79 of the optical fiber 18 which is mounted and positioned by a precision positioner 82. Light, e.g. fluorescence, originating in the reaction chamber 26 follows a reverse path out of the chamber 26 along the optical fiber 18 and is partially reflected by the beam splitter 78 as a beam 84 to the detector means 86. The detector means 86 is sensitive to at least the wavelength of the fluorescence beam 84 and outputs a detection signal that is proportional to the amplitude of the fluorescence beam 84. The detection signal is output to a processing means 88 such as, for example, a computer, where the signal is processed to obtain the information desired.

In operation of one embodiment of the invention, the probe 12 is inserted into a reservoir of the fluid of interest so that the fluid end 22 of the fritted member 20 is positioned in the region of the fluid to be tested. The means 70 for withdrawing fluid is operated to draw fluid from the reservoir through the fritted member 20 into the reaction chamber 26 and through the aspiration conduit 40 past the T-shaped connector 66. A reagent, for example, an antibody, previously prepared by binding to an inert solid phase support such as, for example, microspheres, is introduced into the reaction chamber 26 from the reagent injection means 50 through the reagent conduit 32. Sufficient reagent is introduced into the reaction chamber 26 to at least cover the interior flat face 29 of the member 20 in the vicinity of the terminal end 42 and the optical fiber 18 with the reagent and its support (i.e. microspheres). The means 72 for returning the fluid is operated to cause only the fluid in the aspiration conduit 40 between the T-shaped connector 66 and the reaction chamber 26 to flow into the reaction chamber 26 and past the reagent thereby forming an affinity reaction product betweeen the reagent and the analyte in the sampling chamber 26. If the affinity reaction product fluoresces, the product is exposed to a beam of light from the optic system 16 and such fluorescence is detected and analyzed by the optic system 16. If the affinity reaction product is not fluorescent, then a second reagent tagged with a label which will fluoresce when excited by a light beam, and also reacts with the analyte, is introduced into the reaction chamber 26 from a second reagent injections means through a second reagent conduit. Excess secondary reagent is removed by rinsing. A pulsed laser beam 76 having a power level of less than about 20 mW, for example, is transmitted from the light source 74 through the beam splitter 78 and the lens 80 onto the optical fiber 18 and into the reaction chamber 26. The laser beam 76 is of a wavelength to excite the affinity product to fluorescence and the fluorescence beam 84 is directed through the optical fiber 18 and the lens 80 to the beam splitter 78 where it is reflected into the detector means 86 which outputs the detection signal that is proportional to the amplitude of the fluorescence beam 84. The detection signal is output to the processing means 88 which determines, for example, the molar concentration of the analyte in the fluid. Thereafter, th entire contents, or selected portions thereof may be removed from the reaction chamber 26 through the waste conduit 36 into the waste removal means 56 and the sensor is regenerated by repeating all or a portion of the above operations.

It will be recognized that the present invention is suitable for a wide variety of modes of operation. For example, the microspheres themselves may be reactive with a moiety in the analyte, or the microspheres may be eliminated and a liquid carrier employed. The reactants may be held within the sampling chamber for a period of incubation or one or more of the reagents may be flowed through the sampling chamber as desired.

Washing of the contents of the reaction chamber may be performed without removing microsphere-bound materials from the reaction chamber, for example, to remove interferants, such washing being most useful under certain reaction circumstances. Other environmental conditions may be developed within the sampling chamber depending upon the desired or sought reaction, as will be recognized by a person skilled in the art.

Whereas a laser light source and an optical fiber waveguide have been described, it is recognized that other light sources and/or waveguides may be employed.

In order to provide a better understanding of the present invention, the following examples are given by way of illustration and not by way of limitation.

EXAMPLE 1

FITC was covalently bound to 6 $\mu$m silica beads and a slurry with a concentration of 8 mg/ml of the beads was prepared. A biosensor was prepared with a reaction chamber having a volume of about 0.5 $\mu$L and 50 $\mu$L of the bead slurry was injected into the reaction chamber. The chamber and the beads were illuminated by a laser beam and the amount of fluorescence was recorded. The chamber was rinsed with 20–30 $\mu$L of water and again illuminated with the laser beam. The fluorescence of the material in the reaction chamber after the rinse was recorded. The beads were then removed from the chamber with a rinse of 50–60 $\mu$L of water and the fluorescence of the chamber was recorded. The procedure was repeated four more times. The results are shown in TABLE 1 and show the reproducibility of introducing affinity beads into the chamber, the ability to keep them within the field of view of the fiber optic while rinsing and the ability to remove them after the measurement is finished, i.e. to regenerate the sensor. The low value for the coefficient of variation (CV) for the combined measurements shows the excellent reproducibility of the system.

TABLE 1

| Measurement | Injection (Signal Level) | Rinse (Signal Level) | Regeneration (Signal Level) |
| --- | --- | --- | --- |
| 0 | — | — | 0.069 |
| 1 | 510 | 510 | 0.078 |
| 2 | 560 | 560 | 0.080 |
| 3 | 470 | 470 | 0.084 |
| 4 | 550 | 550 | 0.086 |
| 5 | 470 | 470 | 0.084 |
| CV | 7.7% | 7.7% | 7.8% |

EXAMPLE 2

The procedure of Example 1 was followed except that 50 $\mu$l of unlabeled 6 $\mu$m silica beads were introduced into the reaction chamber followed by 20 $\mu$l of a 100 $\mu$M solution of FITC in water. The results are shown in TABLE 2. The repeatability from run to run showed the regenerability of the sensor as it did in Example 1. The lowering of the signal level after the first rinse shows the small level of affinity of the FITC for the untreated beads. As in Example 1, the low value for CV demonstrates the ability to regenerate the sensor.

TABLE 2

| Measurement | Injection (Signal Level) | Rinse (Signal Level) |
| --- | --- | --- |
| 0 | — | 3.78 |

TABLE 2-continued

| Measurement | Injection (Signal Level) | Rinse (Signal Level) |
|---|---|---|
| 1 | 25.2 | 3.70 |
| 2 | 25.2 | 3.83 |
| 3 | 25.3 | 3.78 |
| 4 | 25.2 | 3.73 |
| 5 | 25.3 | 3.78 |
| CV | 0.6% | 1.2% |

EXAMPLE 3

A biosensor was prepared with a reaction chamber having an approximate volume of 0.5 μl. Three test solutions were prepared: Solution A of 100 μM sodium fluorescein in water; Solution B of 5 mg/ml of FITC-labeled IgG immunoglobulin in water with a concentration of 140 μM FITC; and Solution C of 5 mg/ml of FITC-labeled IgG in human blood serum with concentration of 140 μM FITC. The reaction chamber was rinsed and the sensor was placed in a test solution. The test solution was aspirated through the reaction chamber and the chamber was again rinsed. The sensor was removed from the solution, rinsed and placed in a fluorescent cell. The aspirated solution was returned through the chamber and out through the fritted member into the cell. The sensor was removed and the solution in the cell was diluted to a constant mark of about 1 ml. The concentration of fluorescent species in the cell was determined by fluorimetry and from that concentration the volume of aspirated material was determined. The test was repeated four more times for each solution. The results are shown in TABLE 3. The low CV values for all of the measurements demonstrates the reproducibility of the aspiration of a solution of such biological importance as blood serum.

TABLE 3

| Measurement | Aspiration volume (μl) | | |
|---|---|---|---|
| | Solution A | Solution B | Solution C |
| 1 | 12.3 | 10.5 | 13.4 |
| 2 | 13.4 | 12.9 | 13.4 |
| 3 | 11.7 | 11.5 | 13.9 |
| 4 | 11.9 | 11.4 | 13.2 |
| 5 | 12.1 | 11.4 | 13.0 |
| CV | 5.4% | 7.5% | 2.5% |

EXAMPLE 4

Figure 5:
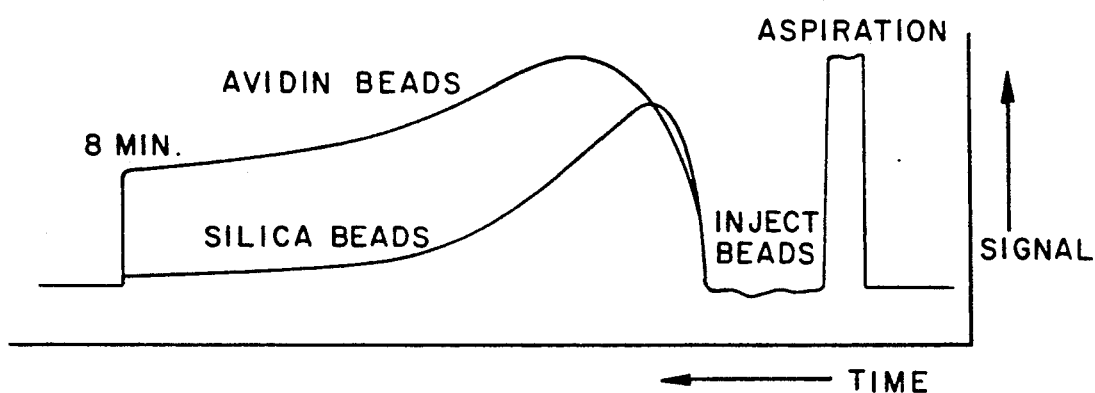
FIG. 5 is time v. signal plot of the fluorescence detected using an embodiment of the present invention width avidin-attached silica beads and blank silica beads in the presence of biotin-FITC (fluorescein isothiocyanate) solution.

Avidin (a glycoprotein affinity reagent for biotin) was covalently bound by a conventional immobilization procedure to 6 μm silica beads and a slurry with a concentration of 7.5 mg/ml of the beads was prepared. A 2 μM test solution was prepared with fluorescein isothiocyanate (FITC) labeled biotin (biotin-FITC) in water. A biosensor was prepared with a reaction chamber having an approximate volume of 0.5 μl and the sensor was immersed in the test solution. A laser light source was energized and a laser light beam was directed into the reaction chamber via an optical fiber. A chopper was installed between the light source and the fiber; the chopper blocked the laser beam for about seven seconds out of every eight seconds in order to minimize the chance of photodegradation of the material in the reaction chamber. A volume of 14 μl of the test solution was aspirated through the reaction chamber as the pulsing of the laser beam was continued. The presence of the biotin-FITC in the chamber was detected by its fluorescence, as is seen in FIG. 5. Fifty microliters of the bead slurry were injected into the reaction chamber with all other capillaries sealed. Since the beads did not have a fluorescence marker attached, FIG. 5 does not show any fluorescent activity. The previously aspirated test solution was reinjected into the reaction chamber and there was an immediate fluorescence detected. The fluorescence peaked after about one minute and then started to trail off slowly with time. After eight minutes, a water rinse of 6 μl/min was introduced into the reaction chamber. As is seen in FIG. 5, the level of fluorescence returned to background. A similar run with untreated silica beads produced a fluorescence signal that trailed off much more quickly. Among other things, this Example demonstrates the general affinity capabilities of the sensor. The coefficient of variation (CV) for the combined affinity assay steps employed in this Example, with 5 repetitions, was less than 5%.

As may be seen from the above, the present invention provides a regenerable fiber optic-based sensor and in particular it provides such a sensor that is useful for in situ analyses. Additionally, the present invention provides for a regenerable fiber optic-based sensor small enough to be placed into a biological system, e.g. through a hypodermic needle. The present invention provides for a means of nearly continuous monitoring the moieties of interest in biological fluids which is in sharp contrast to the prior means for measuring those moieties in situ.

Although particular embodiments of the invention have been discussed, it will be understood that these are examples that were described for the purposes of illustration and that the invention is capable of numerous rearrangements, modifications and substitutions of parts without departing from the spirit of the invention.

Various of the features of the invention which are believed to be new are set forth in the appended claims.

What is claimed is:

1. A regenerable microscale biosensor comprising:
   a. probe means suitable for disposal in situ of a body site containing a suspect analyte in a fluid, said probe means including:
      i. optical fiber means having a first end thereof terminating within said probe means and its opposite end terminating remote from said probe means;
      ii. a plurality of capillary conduits having a first of their respective ends terminating within said probe means and their respective opposite ends terminating remote from said probe means;
      iii. said first ends of said optical fiber means and said capillary conduits terminating in a substantially common plane;
      iv. fritted means porous to said fluid and said suspect analyte defining a cover for said first ends of said optical fiber and said capillary conduits and including an inner wall spaced from said first ends and defining a reaction chamber between said first ends and said cover wherein said first ends of said optical fiber and said capillary conduits are in communication with said reaction chamber; and
      v. fluid permeable means covering the first end of at least one of said capillary conduits within said reaction chamber;
   b. optical means disposed remotely of said probe means and including i. a source of radiant energy in communication with that end of said optical fiber remote from said probe means;

ii. means for detecting radiant energy emanating from said reaction chamber through said optical fiber, and iii. means for converting said emanating radiant energy to a visual indication of the presence of said suspect analyte within said reaction chamber; and c. means disposed remote from said probe means and communicating with respective ones of the ends of said capillary conduits terminating remote from said probe means for selectively introducing and removing materials into and out of said reaction chamber via said capillary conduits during the in situ disposal of the probe means at the body site, including means for selectively developing vacuum conditions within said reaction chamber for selectively withdrawing the contents of said reactive chamber without withdrawal of said probe means from its in situ body site wherein said reaction chamber is constructed so as to receive further analyte and further materials from a location remote from said reaction chamber without withdrawal of said probe from its in situ body site.

2. The biosensor of claim 1 further including a source of mobile particulates in a fluid medium, wherein said particulates are suitable for transfer into said reaction chamber via one of said capillary conduits.

3. The biosensor of claim 2 wherein said particulates comprise microspheres having an average particle size of less than about 7 $\mu$m.

4. The biosensor of claim 2 wherein said particulates comprise an inert substance bearing a coating of an antibody.

5. The biosensor of claim 1 further including a means for aspirating said analyte through said reaction chamber comprising:

means for withdrawing said analyte through said reaction chamber from said body site;

means for returning said analyte through said reaction chamber to said body site; and connecting means having a plurality of connectors for selectively connecting said remote end of at least one of said capillary conduits with at least said means for withdrawing and said means for returning whereby a quantity of said analyte is drawn from said body site, through said fritted means, through said reaction chamber, through said at least one of said conduits and through said connecting means to said means for withdrawing and a reproducible quantity of said analyte is returned from said connecting means through said conduit, through said reaction chamber and to said body site by said means for returning said analyte.

* * * * *

UNITED STATES PATENT AND TRADEMARK OFFICE
CERTIFICATE OF CORRECTION

PATENT NO. : 5,176,881

DATED : January 5, 1993

INVENTOR(S) : Michael J. Sepaniak and Tuan Vo-Dinh

It is certified that error appears in the above-identified patent and that said Letters Patent is hereby corrected as shown below:

At column 5, line 67, delete "ob" and insert -- of --.

At Column 7, line 41, after "reagent" delete "injections" and insert -- injection --

Signed and Sealed this

Twenty-eighth Day of December, 1993

Attest:

BRUCE LEHMAN

Attesting Officer

Commissioner of Patents and Trademarks